United States Patent
Noguchi

[11] Patent Number: 5,842,151
[45] Date of Patent: Nov. 24, 1998

[54] PREDICTION METHOD AND APPARATUS FOR A SECONDARY STRUCTURE OF PROTEIN

[75] Inventor: Tamotsu Noguchi, Kawasaki, Japan

[73] Assignee: Fujitsu Limited, Kawasaki, Japan

[21] Appl. No.: 679,099

[22] Filed: Jul. 12, 1996

[30] Foreign Application Priority Data

Dec. 8, 1995 [JP] Japan .................................. 7-320911

[51] Int. Cl.[6] ...................................................... G06F 19/00
[52] U.S. Cl. .............................................. 702/27; 702/19
[58] Field of Search .................................. 364/496, 497, 364/499; 395/924, 911; 436/89, 86, 90; 530/300, 337, 350; 702/27, 19

[56] References Cited

U.S. PATENT DOCUMENTS 5,612,895  3/1997  Balaji et al. ............................ 364/496

OTHER PUBLICATIONS

Thornton et al. "Pediction of Protein Secondary Structure Using a Combined Method Based on the Recognition, Lim and Garnier–Osguthorpe–Robson Algorithms" Journal of Molecular Structure (Theochem) 232 (1991) pp. 321–336.

Riss et al. "Improving Prediction of Protein Secondary Structure Using Structured Neurl Networks and Multiple Sequence Alignments" Journal of Computational Biology v.3 n.1, 1996, pp. 163–183.

Primary Examiner—Melanie Kemper
Attorney, Agent, or Firm—Staas & Halsey

[57] ABSTRACT

A prediction method and apparatus for secondary structures of a protein in which accuracy in prediction of a formation of a β-sheet is increased and which can applied to any type of protein including an α-helix and a β-sheet. Formation of the α-helix is predicted with respect to each amino acid residue in a sequence of amino acid residues. Then, formation of the β-sheet is predicted with respect to all pairs of residues which were not predicted to form the α-helix. Results of prediction of the α-helix and the β-sheet are combined to obtain a result of prediction of the secondary structure of the protein.

16 Claims, 17 Drawing Sheets

FIG. 5

| RESIDUE(j) | -6 | -5 | -4 | -3 | -2 | -1 | 0 | +1 | +2 | +3 | +4 | +5 | +6 |
|---|---|---|---|---|---|---|---|---|---|---|---|---|---|
| A | 0.14 | 0.25 | 0.61 | 0.30 | 0.71 | 0.29 | 0.60 | 0.32 | 0.10 | 0.32 | 0.19 | 0.21 | -0.09 |
| C | -0.26 | -0.20 | 0.00 | 0.02 | -0.11 | 0.20 | -0.13 | -0.02 | -0.10 | -0.22 | -0.15 | -0.22 | -0.29 |
| D | 0.04 | 0.15 | 0.31 | 0.11 | -0.11 | 0.02 | -0.44 | -0.45 | -0.70 | -0.82 | -0.55 | -0.29 | -0.22 |
| E | -0.06 | 0.20 | 0.55 | 0.31 | 0.44 | 0.21 | 0.23 | 0.23 | 0.12 | 0.04 | -0.24 | -0.26 | -0.19 |
| F | 0.04 | 0.11 | -0.02 | 0.22 | 0.09 | 0.19 | 0.01 | 0.42 | 0.16 | 0.12 | 0.09 | -0.08 | 0.06 |
| G | -0.06 | -0.40 | -0.08 | -0.62 | -0.71 | -0.80 | -0.73 | -0.42 | -0.40 | -0.42 | -0.16 | -0.42 | -0.11 |
| H | 0.04 | 0.14 | -0.21 | 0.01 | -0.07 | -0.02 | 0.04 | -0.35 | 0.05 | -0.12 | 0.35 | -0.04 | -0.28 |
| I | -0.06 | 0.10 | -0.15 | -0.21 | -0.06 | -0.01 | 0.02 | -0.33 | 0.02 | -0.14 | 0.34 | -0.06 | 0.00 |
| K | -0.04 | 0.05 | -0.12 | 0.60 | 0.32 | 0.10 | 0.10 | 0.32 | 0.19 | 0.14 | 0.25 | 0.61 | 0.30 |
| L | -0.26 | 0.02 | -0.14 | 0.13 | -0.02 | -0.10 | -0.10 | 0.22 | 0.15 | 0.26 | 0.20 | 0.00 | 0.02 |
| M | -0.35 | 0.19 | 0.14 | 0.44 | 0.45 | 0.70 | -0.70 | -0.82 | -0.55 | 0.04 | 0.15 | 0.31 | 0.11 |
| N | -0.33 | -0.21 | -0.22 | -0.42 | -0.32 | -0.19 | 0.12 | 0.04 | -0.24 | -0.06 | 0.20 | 0.55 | -0.02 |
| P | 0.32 | -0.26 | -0.14 | 0.07 | -0.04 | -0.76 | -1.12 | -1.89 | -1.44 | -1.31 | -1.02 | -0.92 | -0.42 |
| Q | -0.15 | -0.08 | 0.06 | 0.12 | 0.12 | 0.19 | -0.21 | 0.11 | -0.37 | -0.02 | -0.21 | -0.06 | -0.01 |
| R | -0.24 | -0.42 | -0.11 | 0.16 | 0.11 | -0.76 | 0.15 | -0.11 | 0.06 | 0.01 | 0.60 | 0.32 | 0.12 |
| S | 0.09 | 0.04 | -0.28 | 0.21 | 0.11 | -0.24 | -0.12 | 0.60 | 0.32 | 0.10 | 0.13 | -0.02 | 0.10 |
| T | -0.16 | -0.06 | 0.00 | 0.15 | 0.60 | -0.09 | -0.14 | -0.13 | 0.02 | -0.10 | 0.44 | 0.45 | 0.71 |
| V | 0.05 | 0.31 | 0.30 | 0.12 | -0.13 | -0.37 | -0.26 | -0.14 | 0.10 | -0.22 | 0.15 | 0.16 | 0.12 |
| W | 0.04 | 0.01 | -0.02 | 0.14 | 0.11 | -0.06 | -0.08 | -0.06 | 0.70 | -0.82 | -0.55 | -0.21 | -0.11 |
| Y | -0.25 | 0.11 | 0.11 | -0.14 | -0.60 | 0.32 | -0.42 | -0.11 | 0.12 | -0.04 | -0.22 | -0.05 | -0.06 |
| - | -0.10 | -0.05 | -0.31 | -0.14 | -0.13 | -0.02 | -0.10 | -0.44 | -0.43 | -0.71 | -0.14 | 0.15 | -0.19 |

Window position

FIG. 6

| RESIDUE(N) | RESIDUE (C) A | C | D | E | F | G | H | I | K | L | M | N | P | Q | R | S | T | V | W | Y |
|---|---|---|---|---|---|---|---|---|---|---|---|---|---|---|---|---|---|---|---|---|
| A | 0.5 | 0.6 | 0.3 | 0.2 | 1.1 | 0.4 | 0.5 | 1.2 | 0.6 | 1.1 | 0.8 | 0.2 | 0.1 | 0.6 | 0.4 | 0.6 | 1.0 | 1.4 | 1.4 | 1.5 |
| C | 2.2 | 8.4 | 0.3 | 0.7 | 3.9 | 0.8 | 0.8 | 2.5 | 4.2 | 1.7 | 1.2 | 0.7 | 0.6 | 0.6 | 0.5 | 3.4 | 1.1 | 2.6 | 1.0 | 2.5 |
| D | 0.2 | 0.2 | 0.2 | 0.2 | 0.2 | 0.3 | 0.8 | 0.5 | 0.7 | 0.2 | 0.3 | 0.3 | 0.3 | 0.5 | 1.2 | 0.6 | 1.2 | 1.1 | 0.4 | 1.0 |
| E | 0.3 | 1.5 | 0.2 | 0.3 | 0.7 | 0.3 | 0.4 | 0.7 | 1.1 | 0.2 | 0.3 | 0.3 | 0.5 | 1.2 | 0.6 | 1.3 | 1.1 | 0.4 | 1.0 | .12 |
| F | 1.1 | 2.8 | 0.4 | 0.5 | 2.9 | 0.8 | 1.0 | 3.2 | 0.6 | 1.9 | 2.1 | 0.4 | 0.5 | 0.9 | 0.9 | 1.1 | 1.0 | 3.1 | 1.9 | 2.4 |
| G | 0.3 | 0.4 | 0.2 | 0.3 | 1.0 | 0.4 | 0.3 | 0.7 | 0.3 | 0.8 | 0.5 | 0.3 | 0.2 | 0.4 | 0.3 | 0.7 | 0.7 | 1.1 | 0.8 | 1.5 |
| H | 0.7 | 1.7 | 0.9 | 1.0 | 1.2 | 0.6 | 1.5 | 0.5 | 0.5 | 0.7 | 0.7 | 0.9 | 0.3 | 0.9 | 1.5 | 1.9 | 2.5 | 1.7 | 1.5 | 1.5 |
| I | 1.3 | 3.5 | 0.4 | 0.6 | 2.1 | 0.6 | 1.1 | 2.8 | 1.1 | 2.4 | 1.6 | 0.5 | 0.5 | 1.4 | 1.2 | 0.8 | 2.2 | 0.8 | 1.1 | 1.9 |
| K | 0.4 | 0.7 | 0.7 | 2.4 | 0.8 | 0.2 | 0.7 | 0.7 | 0.6 | 0.5 | 0.4 | 0.4 | 0.6 | 1.3 | 0.5 | 0.9 | 1.2 | 2.3 | 1.4 | 2.5 |
| L | 1.0 | 2.2 | 0.3 | 0.4 | 1.7 | 0.8 | 0.4 | 2.3 | 0.5 | 1.6 | 2.6 | 0.4 | 0.3 | 0.9 | 0.7 | 0.8 | 0.9 | 2.3 | 1.3 | 2.1 |
| M | 0.5 | 0.6 | 0.3 | 0.2 | 1.1 | 0.4 | 0.5 | 1.2 | 0.6 | 1.1 | 0.8 | 0.2 | 0.1 | 0.6 | 0.4 | 0.6 | 1.0 | 1.4 | 1.4 | 1.5 |
| N | 2.2 | 8.4 | 0.3 | 0.7 | 3.9 | 0.8 | 0.8 | 2.5 | 4.2 | 1.7 | 1.2 | 0.7 | 0.6 | 0.6 | 0.5 | 3.4 | 1.1 | 2.6 | 1.0 | 2.5 |
| P | 0.2 | 0.2 | 0.2 | 0.2 | 0.2 | 0.3 | 0.8 | 0.5 | 0.7 | 0.2 | 0.3 | 0.3 | 0.3 | 0.5 | 1.2 | 0.6 | 1.2 | 1.1 | 0.4 | 1.0 |
| Q | 0.3 | 1.5 | 0.2 | 0.3 | 0.7 | 0.3 | 0.4 | 0.7 | 1.1 | 0.2 | 0.3 | 0.3 | 0.5 | 1.2 | 0.6 | 1.3 | 1.1 | 0.4 | 1.0 | .12 |
| R | 1.1 | 2.8 | 0.4 | 0.5 | 2.9 | 0.8 | 1.0 | 3.2 | 0.6 | 1.9 | 2.1 | 0.4 | 0.5 | 0.9 | 0.9 | 1.1 | 1.0 | 3.1 | 1.9 | 2.4 |
| S | 0.3 | 0.4 | 0.2 | 0.3 | 1.0 | 0.4 | 0.3 | 0.7 | 0.3 | 0.8 | 0.5 | 0.3 | 0.2 | 0.4 | 0.3 | 0.7 | 0.7 | 1.1 | 0.8 | 1.5 |
| T | 0.7 | 1.7 | 0.9 | 1.0 | 1.2 | 0.6 | 1.5 | 0.5 | 0.5 | 0.7 | 0.7 | 0.9 | 0.3 | 0.9 | 1.5 | 1.9 | 2.5 | 1.7 | 1.5 | 1.5 |
| V | 1.3 | 3.5 | 0.4 | 0.6 | 2.1 | 0.6 | 1.1 | 2.8 | 1.1 | 2.4 | 1.6 | 0.5 | 0.5 | 1.4 | 1.2 | 0.8 | 2.2 | 0.8 | 1.1 | 1.9 |
| W | 0.4 | 9.7 | 0.7 | 2.4 | 0.8 | 0.2 | 0.7 | 0.7 | 0.6 | 0.5 | 0.4 | 0.4 | 0.6 | 1.3 | 0.5 | 0.9 | 1.2 | 2.3 | 1.4 | 2.5 |
| Y | 1.2 | 3.2 | 0.5 | 1.0 | 1.7 | 3.2 | 1.0 | 1.1 | 2.3 | 1.6 | 2.5 | 1.8 | 0.9 | 0.9 | 1.2 | 1.6 | 1.0 | 2.7 | 2.3 | 4.0 |

> α-lytic protease
ANIVGGIEYSINNASLCSVGFSVTRGATKGFVTAGHCGTVNATARIGGAVVGTFAARVFPGNDRAWVSLT
SAQTLLPRVANGSSFVTVRGSTEAAVGAAVCRSGRTTGYQCGTITAKNVTANYAEGAVRGLTQGNACMGR
GDSGGSWITSAGQAQGVMSGGNVQSNGNNCGIPASQRSSLFERLQPILSWYGLSLVTG

FIG. 8

```
α-lytic protease
number of residues : 198

HELIXPT..
SHEETPR..        EEEE      EEE   EEE   EEEE EEEEEE           EEEE EEEE EEEE
FINALPR..        EEEE      EEE   EEE   EEEE EEEEEE           EEEE EEEE EEEE      EEE
SUMMARY..        EEEE      EEE   EEEE  EEEE EEEEEE           EEEEEEEEE EEEE      EEE              EEEEEE
SEQUENCE.   ANIVGGIEYSINNASLCSVGFSVTRGATKGFVTAGHCGTVNATARIGGAVVGTFAARVFPGNDRAWVSLTSAQTLLPRVA
                 +    *    +    *    +    *    +    *    +    *    +    *    +    *    +    *

HELIXPT..                         HHHHHHH                        HHHHHHH
SHEETPR..        EEEE             EEEE               EEEEEEEEEEEEEEE       EEEEEE              EEE   EEEEE
FINALPR..        EEEE        HHHHHHHHEEEE            EEEEEEEEEEEEEEEHHHHHHHHEEEEEE              EEE   EEEEE
SUMMARY..     E  EEEE             EEEE               EEEEEEEEEEEEEEE       EEEEEE              EEE   EEEEEEE
SEQUENCE.   NGSSFVTVRGSTEAAVGAAVCRSGRTTGYQCGTITAKNVTANYAEGAVRGLTQGNACMGRGDSGGSWITSAGQAQGVMSG
                 +    *    +    *    +    *    +    *    +    *    +    *    +    *    +    *

HELIXPT..                 HHHHHH
SHEETPR..         EEEE    EEEE    EE
FINALPR..         EEEE    HHHHHH   EE
SUMMARY..    E    EEEEEHHHHHHHHHH  EE
SEQUENCE.   GNVQSNGNNCGIPASQRSSLFERLQPILSWYGLSLVTG
                 +    *    +    *    +    *
```

FIG. 14

```
>1LFI01         691
HELIXPT..               HHHHHHHH HHHHHHH              HHHHHH
SUMMARY..      EEEE    HHHHHHHHHHHHHHH    EEEE     HHHHHHHH        EEEE
SEQUENCE.  GRRRSVQWCAVSNPEATKCFQWQRNMRKVRGPPVSCIKRDSPIQCIQAIAENRADAVTLD

HELIXPT..  HHHHHH
SUMMARY..  HHHHHHHH     EEE EEEEEE     EE EEEEEEEEE                 EEE
SEQUENCE.  GGFIYEAGLAPYKLRPVAAEVYGTERQPRTHYYAVAVVKKGGSFQLNELQGLKSCHTGLR

HELIXPT..        HHHHHHHH         HHHH              HHHHHH
SUMMARY..         HHHHHHH         HHHHHH    EE      HHHH
SEQUENCE.  RTAGWNVPIGTLRRFLNWTGPPEPIEAAVARFFSASCVPGADKGQFPNLCRLCAGTGENK
```

FIG. 17

```
>1LF101        691
HELIXPT..            HHHHHHHH HHHHHH              HHHHHH
SHEETPR.     EEEE                       EEEE                     EEE
FINALPR..    EEEE    HHHHHHHH HHHHHH    EEEE       HHHHHH        EEE
SUMMARY..    EEEE    HHHHHHHHHHHHHH     EEEE       HHHHHHHH      EEEE
SEQUENCE. GRRRSVQWCAVSNPEATKCFQWQRNMRKVRGPPVSCIKRDSPIQCIQAIAENRADAVTLD

HELIXPT.. HHHHHH
SHEETPR.              EEE  EEEE    EE   EEEE                EEE
FINALPR.. HHHHHH      EEE  EEEE    EE   EEEE                EEE
SUMMARY.. HHHHHHHH    EEE EEEEEE   EE EEEEEEEEE             EEE
SEQUENCE. GGFIYEAGLAPYKLRPVAAEVYGTERQPRTHYYAVAVVKKGGSFQLNELQGLKSCHTGLR

HELIXPT..    HHHHHHHH         HHHH              HHHHHH
SHEETPR.                                 EE
FINALPR..    HHHHHHHH         HHHH       EE     HHHHHH
SUMMARY..    HHHHHHH         HHHHHH      EE     HHHH
SEQUENCE. RTAGWNVPIGTLRRFLNWTGPPEPIEAAVARFFSASCVPGADKGQFPNLCRLCAGTGENK
```

PREDICTION METHOD AND APPARATUS FOR A SECONDARY STRUCTURE OF PROTEIN

BACKGROUND OF THE INVENTION

1. Field of the Invention

The present invention generally relates to a prediction method and apparatus for a secondary structure of a protein and, more particularly, to a prediction method and apparatus for a secondary structure of a protein such as an α-helix or a β-sheet which is a characteristic structure of protein.

A tertiary structure of a protein can be identified by prediction of a secondary structure of the protein. It is necessary to identify a tertiary structure of a protein in a development of medicine. For example, it is necessary to identify the tertiary structure of a receptor protein when a docking simulation is performed on a molecule of drug and an active site of the protein. Such a simulation is performed to investigate as to which part of a sequence of residues, which is a sequence of molecules of the protein, will be docking with the drug. If the tertiary structure is known, the drug design will be possible.

Generally, a protein has a characteristic stereo-helical structure which is inherent in protein. Such a helical structure comprises secondary structures referred to as an α-helix or a β-sheet. A tertiary structure of a protein can be identified if the secondary structure of the protein is analyzed. Thus, it is desired to develop a method for analyzing a tertiary structure of a protein by predicting the secondary structure of the protein in a simple manner.

2. Description of the Related Art

Many studies have been made through various approaches with respect to prediction of a tertiary structure of a protein, which is one of the most important studies in the protein research field. However, this issue is very difficult to solve, and thus no solution has been given yet. If this issue could be solved, a tertiary structure of a protein may be identified to a certain extent prior to analyzing the tertiary structure by an X-ray analysis or a nuclear magnetic resonance analysis (NMR) in a medical and biological field and so on.

The prediction of the secondary structure of a protein is not based on a direct prediction of the tertiary structure from an amino acid residue sequence, but is a first step of an approach to identify the tertiary structure by predicting a characteristic structure as shown in FIG. 1. If the secondary structure is recognized with a high accuracy, the tertiary structure of the protein can be identified. Accordingly, the accuracy of the prediction of the secondary structure is an important factor of the approach for identifying the tertiary structure of the protein from the secondary structure.

Various approaches for predicting the secondary structure of a protein have been attempted thus far since the "Chous-Fasman" method was revealed in 1974. Presently, the prediction of the secondary structure is performed based on results of various experiments.

For example, the automatic determination method by Kabsch-Sander can identify the secondary structure (each helix of $3_{10}$, α, π; β-sheet; 3, 4 and 5 turns). Additionally, this method can identify a position of an S—S bond. When this method is used, it must be confirmed whether or not the defined secondary structure is appropriate by investigating whether the crystal analysis data to be used was obtained based on more than a predetermined resolution, or by comparing with a secondary structure registered in the protein data bank (PDB).

FIG. 2 is an illustration showing a tertiary structure of a protein. This tertiary structure can be produced by obtaining tertiary coordinates by performing experiments using an X-ray crystallographic analysis or an NMR analysis. In this figure, a represents a bond of residue of the protein, and A to I represent β-strands in the β-sheet. In such a structure, the secondary structure is predicted by information with respect to amino acids surrounding all sequences. In this predicting method, the structure of an α-helix b can be predicted with high accuracy since it is considered that the structure of the α-helix is formed due to an interaction between amino acids adjacent to the sequence.

The prediction of the structure of a protein based on the β-sheet is a method to produce a tertiary structure using plane sheets having no distortion as shown in FIG. 3. When the prediction is performed based on the β-sheet, the structure is predicted by interrelationship between amino acid residues in longitudinal directions shown by arrows in FIG. 3.

However, in the conventional prediction method of the protein secondary structure, the accuracy of prediction is less than 70% in average. This is because the secondary structure is predicted based on only information of amino acid residues adjacent to the sequence. Thus, as mentioned above, the structure of an α-helix can be predicted with high accuracy. However, accuracy in the prediction of the structure of a β-sheet is much lower than the accuracy in the prediction of the α-helix. This is because the structure of the β-sheet is formed based on a hydrogen bond with amino acid residues spaced from the sequence. That is, since the structure of the β-sheet is formed with an interaction with not only residues adjacent to the sequence but also residues in the tertiary, the accuracy of the prediction of the β-sheet falls to as low as 50% to 60%. This results in a low accuracy in the prediction of the entire secondary structure of the protein.

When only the α-helix is concerned, the accuracy in the prediction is more than 80% since the helical structure is determined based on only adjacent amino acid residues. Accordingly, if the accuracy in the prediction of the β-sheet is improved, the accuracy in the prediction of the entire secondary structure can be improved. As discussed above, since the accuracy for the α-helix is high and the accuracy for the β-sheet is low, an accurate prediction cannot be made especially for a protein having a β-sheet, that is, a protein other than an ALL-α protein. Accordingly, there is a problem in that a tertiary structure cannot be predicted due to poor accuracy in the prediction of the secondary structure.

SUMMARY OF THE INVENTION

It is a general object of the present invention to provide an improved and useful prediction method and apparatus for a secondary structure of a protein.

A more specific object of the present invention is to provide a prediction method and apparatus for a secondary structure of a protein in which an accuracy in prediction of a β-sheet is increased so as to increase the overall accuracy in prediction of the secondary structure of a protein.

Another object of the present invention is to provide a prediction method and apparatus for secondary structure of a protein which can be applied to any type of protein such as an ALL-α protein, an ALL-β protein, an α/β protein or an α+β protein.

In order to achieve the above-mentioned objects, there is provided according to one aspect of the present invention a method for predicting secondary structures which are characteristic structures of a protein including an α-helix and a β-sheet, comprising the steps of:

a) predicting a formation of the α-helix with respect to each amino acid residue in a sequence;

b) predicting formation of the β-sheet with respect to all pairs of amino acid residues which were not predicted to form the α-helix by the step a); and c) combining results obtained by the step a) and step b) to obtain a result of prediction of the secondary structures of the protein.

According to this invention, a prediction of formation of the β-sheet is performed on the amino acid residues which were determined not to form the α-helix. Thus, the number of amino acid residues to be analyzed to determine whether each amino acid residue forms the β-sheet is reduced prior to performing the prediction of formation of the β-sheet. That is, the amino acid residues which are not predicted to form the α-helix are automatically rendered to be candidates for determining the formation of the β-sheet. This structure increases an accuracy in prediction of the β-sheet.

In one embodiment according to the present invention, the step a) may comprise the steps of:

a-1) learning which types of amino acid residues have a tendency to form the α-helix;

a-2) determining the formation of the α-helix with respect to each amino acid residue in the sequence based on results obtained by step a-1); and a-3) providing a mark to each amino acid residue which was determined to form the α-helix by step a-2), and subjecting all of the amino acid residues determined not to form the α-helix by step a-2) to the prediction of the β-sheet.

Accordingly, an α-helix formation index can be calculated in a simple manner since the tendency of formation of the α-helix is learned previously. Thus, the determination as to whether or not the α-helix is formed with respect to each amino acid residue can be made in a simple manner.

A determination of step a-2) may be made based on consecutiveness of the amino acid residues having a predetermined level of formability of the α-helix. The consecutiveness of the amino acid residues may be determined based on a series of amino acid residues comprising four amino acid residues.

Additionally, in one embodiment of the present invention, the step b) may comprise the steps of:

b-1) determining a β-sheet tendency index with respect to all pairs of amino acid residues which were not predicted to form the α-helix by the step a);

b-2) selecting candidate residues forming the β-sheet by comparing the β-sheet tendency index with a predetermined threshold value, amino acid residues of a pair having a β-sheet tendency index greater than the threshold value being selected as the candidate residues; and b-3) seeking a series of candidate residues comprising a maximum number of candidate residues from among the candidate residues selected by step b-2) so that the series of candidate residues is determined to form the β-sheet.

In this invention, since the candidate residues are selected before determination of the formation of the β-sheet is made, the determination process is easy and provides a high accuracy.

Additionally, in step b-3), when less than a predetermined number of consecutive residues is not selected as the candidate residues, the non-selected consecutive residues may be regarded as the residues forming the β-sheet. This structure may correct errors included in parameters used for determining the formation of the β-sheet.

Additionally, there is provided according to another aspect of the present invention an apparatus for predicting secondary structures which are characteristic structures of a protein including an α-helix and a β-sheet, the apparatus comprising:

α-helix predicting means for predicting a formation of the α-helix with respect to each amino acid residue in a sequence;

β-sheet predicting means for predicting a formation of the β-sheet with respect to all pairs of amino acid residues which were not predicted to form the α-helix by the α-helix predicting means; and combining means for combining results obtained by the α-helix predicting means and the β-sheet predicting means to obtain a result of prediction of the secondary structure of the protein.

According to this invention, a prediction of formation of the β-sheet is performed on the amino acid residues which were determined not to form the α-helix. Thus, the number of residues to be analyzed to determine whether each residue forms the β-sheet is reduced prior to performing the prediction of the formation of the β-sheet. That is, the residues which are not predicted to form the α-helix are automatically rendered to be candidates for determining the formation of the β-sheet. This structure increases an accuracy in prediction of the β-sheet.

In one embodiment according to the present invention, the α-helix predicting means may comprise:

learning means for learning which types of residues have a tendency to form the α-helix;

determining means for determining the formation of the α-helix with respect to each amino acid residue in the sequence based on results obtained by the learning means; and providing means for providing a mark to each residue which was determined to form the α-helix by the determining means, and subjecting all of the residues determined not to form the α-helix by the determining means to the prediction of the β-sheet.

Accordingly, an α-helix formation index can be calculated in a simple manner since the tendency of formation of the α-helix is learned previously. Thus, the determination as to whether or not the α-helix is formed with respect to each residue can be made in a simple manner.

A determination by the determining means may be made based on consecutiveness of the residues having a predetermined level of formability of the α-helix. The consecutiveness of the residues may be determined based on a series of residues comprising four residues.

Additionally, in one embodiment of the present invention, the β-sheet predicting means may comprise:

determining means for determining a β-sheet tendency index with respect to all pairs of residues which were not predicted to form the α-helix by the α-helix predicting means;

selecting means for selecting candidate residues forming the β-sheet by comparing the β-sheet tendency index with a predetermined threshold value, residues of a pair having a β-sheet tendency index greater than the threshold value being selected as the candidate residues; and seeking means for seeking a series of candidate residues comprising a maximum number of candidate residues from among the candidate residues selected by the selecting means so that the series of candidate residues are determined to form the β-sheet.

In this invention, since the candidate residues are selected before determination of the formation of the β-sheet is made, the determination process is easy and provides a high accuracy.

Additionally, when less than a predetermined number of consecutive residues are not selected as the candidate residues, the non-selected consecutive residues may be regarded as the residues forming the β-sheet. This structure may correct errors included in parameters used for determining the formation of the β-sheet.

Other objects, features and advantages of the present invention will become more apparent from the following detailed description when read in conjunction with the accompanying drawings.

BRIEF DESCRIPTION OF THE DRAWINGS

FIG. 5 is an illustration of contents of an α parameter file shown in FIG. 4;

FIG. 6 is an illustration of contents of a β parameter file shown in FIG. 4;

FIG. 7 is an illustration of contents of a sequence file shown in FIG. 4;

FIG. 8 is an illustration of contents of a result file shown in FIG. 4;

FIG. 14 is an illustration for explaining a result of prediction of the α-helix;

FIG. 17 is an illustration for explaining an output operation of the secondary structure prediction result.

DETAILED DESCRIPTION OF THE PREFERRED EMBODIMENTS

In a prediction of the secondary structure of a protein, the prediction of a β-sheet must be performed based on information with respect to pairs of amino acid residues and residues adjacent to the pairs of amino acid residues. Thus, the prediction of the secondary structure of the protein is performed in such a manner that a prediction of an α-helix is performed first, and then a tendency index of formation of a β-sheet is calculated with respect to pairs of amino acid residues in the remaining domains.

Figure 1:
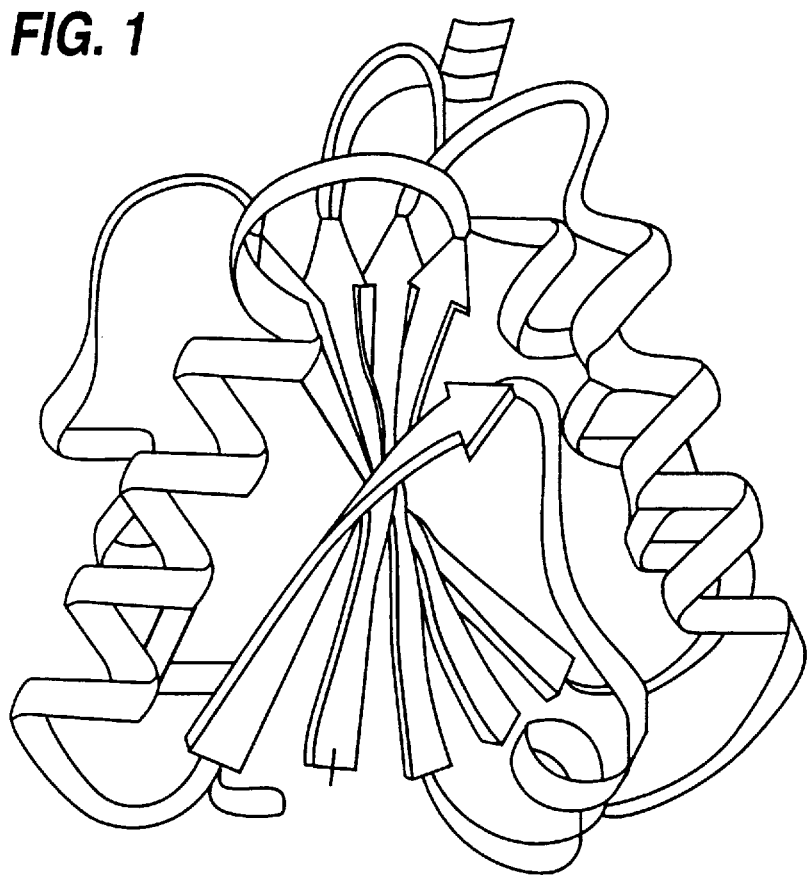
FIG. 1 is an illustration of a structure of a protein.
Figure 2:
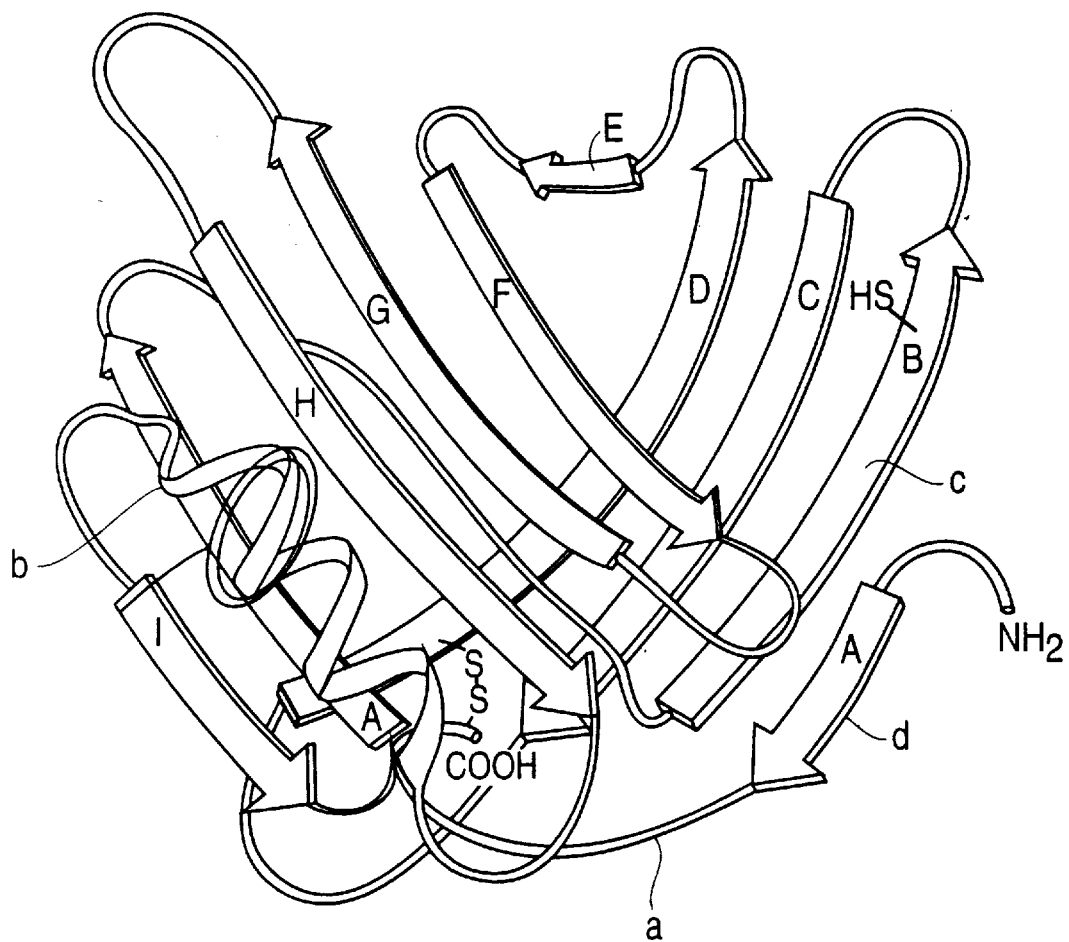
FIG. 2 is an illustration of a structure of protein for explaining a structure of an α-helix.
Figure 3:
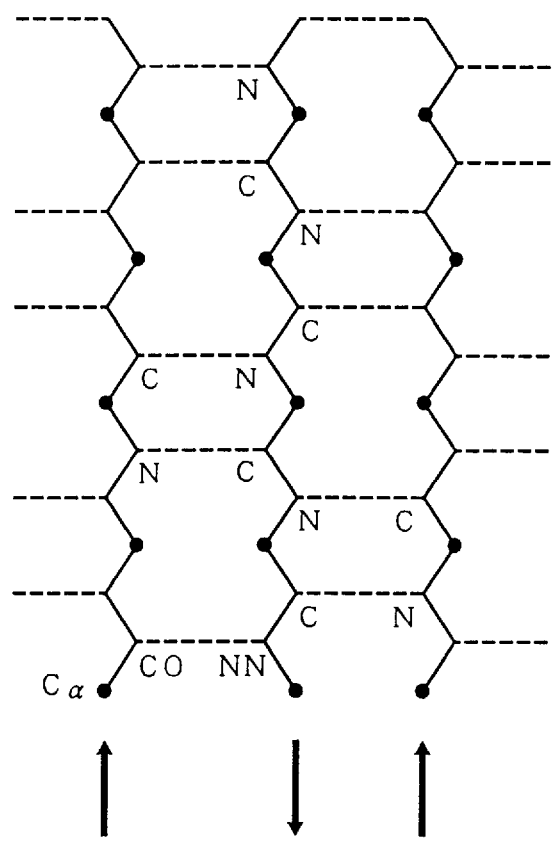
FIG. 3 is an illustration for explaining a structure of a β-sheet.
Figure 4:
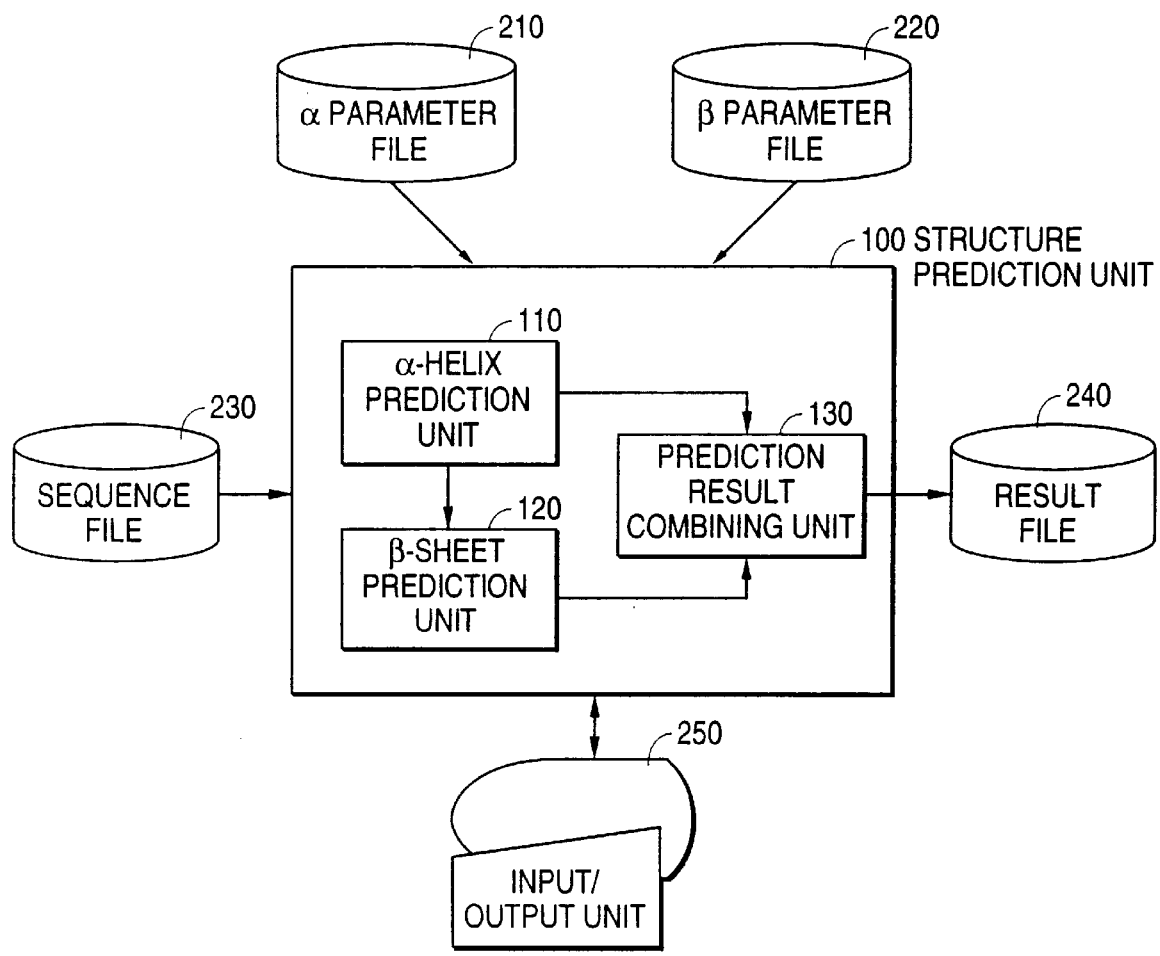
FIG. 4 is a block diagram of a secondary structure prediction system according to an embodiment of the present invention.

FIG. 4 is a block diagram of a secondary structure prediction system according to an embodiment of the present invention.

The secondary structure prediction system shown in FIG. 4 includes a structure prediction unit 100, an α parameter file 210, a β parameter file 220, a sequence file 230, a result file 240 and an input/output unit 250.

The α parameter file 210 stores, as shown in FIG. 5, tendency data of an α-helix in sequential positions between "−6" and "+6" with "0" in the center thereof for each amino acid residue. The prefix "−" represents an N terminal side, and the prefix "+" represents a C terminal side. The β parameter file 220 stores, as shown in FIG. 6, vales representing a tendency of bonding for each amino acid residue. The vertical axis represents residues on the N terminal side, and the horizontal axis represents residues on the C terminal side. The N terminal means an $NH_2$ terminal, and the C terminal means a carboxyl terminal.

The sequence file 230 retains sequence data of amino acid residues as shown in FIG. 7. The result file 240 stores data obtained by combining results of predictions with respect to the α-helix and the β-sheet which results are obtained by the structure prediction unit 100.

The structure prediction unit 100 comprises an α-helix prediction unit 110, a β-sheet prediction unit 120 and a prediction result combining unit 130.

The α-helix prediction unit 110 reads the residue sequence data of a protein stored in the sequence file 230 and contents of the α parameter file 210. The α-helix prediction unit 110 then compares each residue sequence datum with corresponding datum of the α-parameter file 210 beginning from the N terminal. Specifically, the α-helix prediction unit 110 searches the α parameter file 210 in accordance with the position of each residue sequence datum with respect to the center residue. The datum of the position of each residue sequence is determined as to how many positions are shifted rearwardly (+) from the center "0" or how many positions are shifted forwardly (−) from the center "0". The α-helix prediction unit 110 then retrieves the weight value of a formation of an α-helix stored in the searched position. Then, the α-helix prediction unit 110 calculates an α-helix formation index of the center residue by using a neural network based on the weight values corresponding to the positions from −6 to 6, and extract the residues having α-helix formation indexes greater than a predetermined value. The α-helix prediction unit 110 determines a residue sequence having four consecutive amino acid residues as a residue sequence forming the α-helix. This provides a prediction result for the α-helix. A residue sequence having equal to or less than three consecutive residues is determined as a residue belonging to a β-sheet, and the residue data is transferred to the β-sheet prediction unit 120.

The β-sheet prediction unit 120 reads the β parameter file 220 in accordance with the residue data transferred from the α-helix prediction unit 110, and obtains a tendency index for each residue based on a round-robin system. For example, if there are residues corresponding to "A, N, I, V, . . . ", it can be observed from the table shown in FIG. 6 that the tendency index between "A" and "N" is "0.2"; the tendency index between "A" and "I" is "1.2"; and the tendency index between "A" and "V" is "1.4". If a predetermined value is set to "1.0" for extracting the β-sheet, the β-sheet to be extracted is a pair of "A" and "I" and a pair of "A" and "V".

If a mark "E", for example, is provided to a pair to be extracted, and a blank " " is provided to a pair not to be extracted, the above-mentioned case is represented as "EE". This is because the first pair of "A" and "N" has a tendency index less than the predetermined value, and thus the mark E is not provided thereto. Accordingly, if there is a residue having a tendency index less that the predetermined value, consecutiveness of marks is interrupted. The β-sheet prediction unit 120 sorts strings of marks beginning from a string having the maximum number of marks. The string of marks having the maximum number of marks is predicted to be the β-sheet.

The prediction result combining unit 130 combines the prediction result of the α-helix prediction unit 110 and the prediction result of the β-sheet prediction result, and outputs the combined result to the result file 240.

Figure 9:
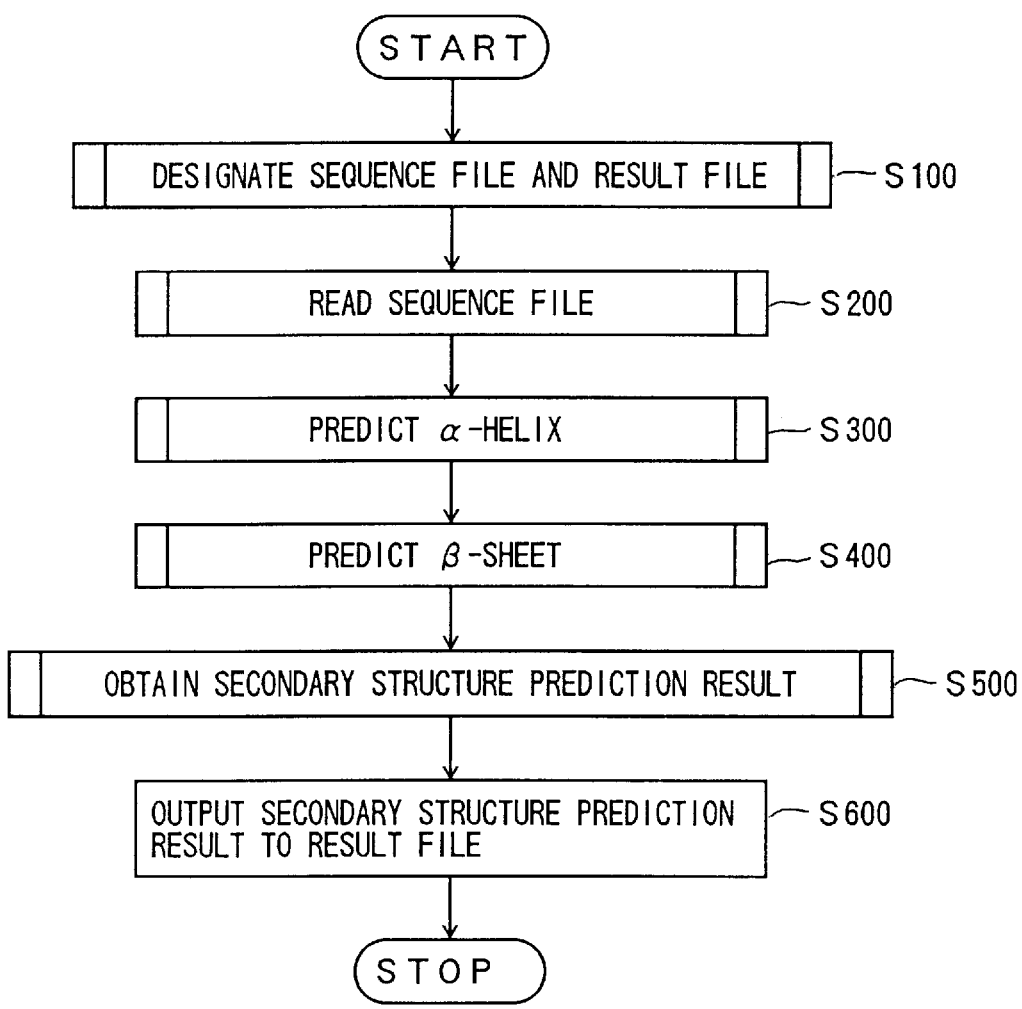
FIG. 9 is a flowchart of an operation performed by a structure prediction unit 100 shown in FIG. 4.

FIG. 9 is a flowchart of an operation performed by the structure prediction unit 100 according to the present embodiment.

When the operation shown in FIG. 9 is started, the input/output unit 250 designates, in step S100, the sequence file 230 and the result file 240 as files to be used by the structure prediction unit 100.

In step S200, the structure prediction unit 100 reads the sequence file 230 to retrieve the sequence data of amino acid residues.

In step S300, the α-helix prediction unit 110 of the structure prediction unit 100 reads the α parameter file 210, and predicts an α-helix in accordance with the sequence data in the sequence file 230. The prediction is performed by using values obtained by an X-ray crystallographic analysis or an NMR analysis as a teaching signal and results obtained by the neural network (back propagation) as data of the α parameter file 210. At this time, only α-helixes are predicted from the sequence of amino acid residues as will be described later.

In step S400, the β-sheet prediction unit 120 of the structure prediction unit 100 reads the β parameter file 220, and predicts a β-sheet as will be described later.

In step S500, the prediction result combining unit 130 of the structure prediction unit 100 combines the α-helix prediction result obtained in step S300 and the β-sheet prediction result obtained in step S400 so as to obtain a secondary structure prediction result.

In step S600, the prediction result combining unit 130 of the structure prediction unit 100 outputs the secondary structure prediction result to the result file 240.

Figure 10:
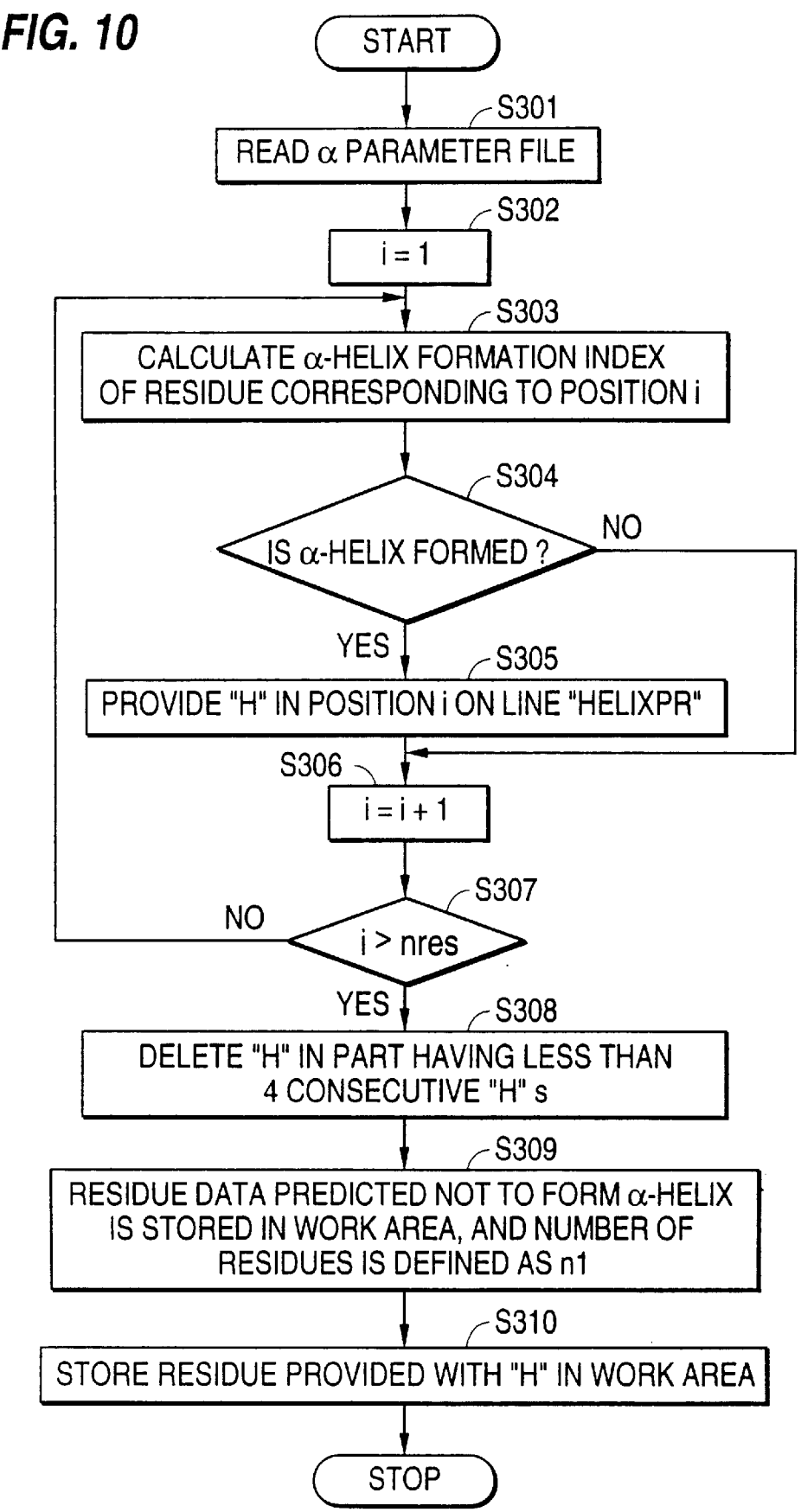
FIG. 10 is a flowchart of an α-helix prediction operation performed by an α-helix prediction unit shown in FIG. 4.

A description will now be given of an operation for prediction of the α-helix in the above-mentioned step S300. FIG. 10 is a flowchart of the α-helix prediction operation performed by the α-helix prediction unit 110.

When the α-helix prediction operation is started, the α-helix prediction unit 110 of the structure prediction unit 100 reads, in step S301, the α parameter file 210. A counter i is set to 1 in step S302. The counter i represents an order of an amino acid residue in the sequence in the sequence file 230.

In step S303, the α-helix formation index corresponding to an amino acid residue located in a position indicated by the counter i is calculated based on the values stored in the α parameter file 210, and the routine proceeds to step S304. It is determined, in step S304, whether or not the amino acid residue forms the α-helix in accordance with the calculated α-helix formation index.

If it is determined, in step S304, that the amino acid residue forms the α-helix, the routine proceeds to step S305.

In step S305, a mark "H" is provided in the i position of the amino acid residue in a helix part of a work area. The mark "H" represents that the α-helix is present in that position. Then, in step S306, the counter i is incremented (i=i+1).

If it is determined, in step S304, that the amino acid residue does not form the α-helix, the routine directly proceeds to step S306.

In step S307, it is determined whether or not the counter i is greater than an entire length "nres" of the sequence of residues. In the example shown in FIG. 7, the entire length "nres" is the number of amino acid residues each of which is represented by a single character. Thus, the entire length "nres" is represented by 198 for the example shown in FIG. 7. If it is determined that the counter i is not greater than the entire length "nres", the routine returns to step S303 since all of the residues have not been investigated. If it is determined that the counter i is greater than the entire length "nres", the routine proceeds to step S308 since all of the residues in the sequence have been investigated.

In step S308, a part, in which a predetermined number of marks "H" are not consecutively provided, is sought in the work area. The part which is not provided with the predetermined number of consecutive marks "H" is determined to be a part corresponding to a residue which does not form the α-helix. Thereafter, the marks "H" corresponding to the above-mentioned part in the work area are deleted.

In step S309, amino acid residues which are predicted as residues which do not form the α-helix are written in another work area. The number of the residues is defined as n1. This value is used in the prediction of the β-sheet.

In step S310, the residue data corresponding to the residues predicted to form the α-helix is stored in the work are.

Figure 11:
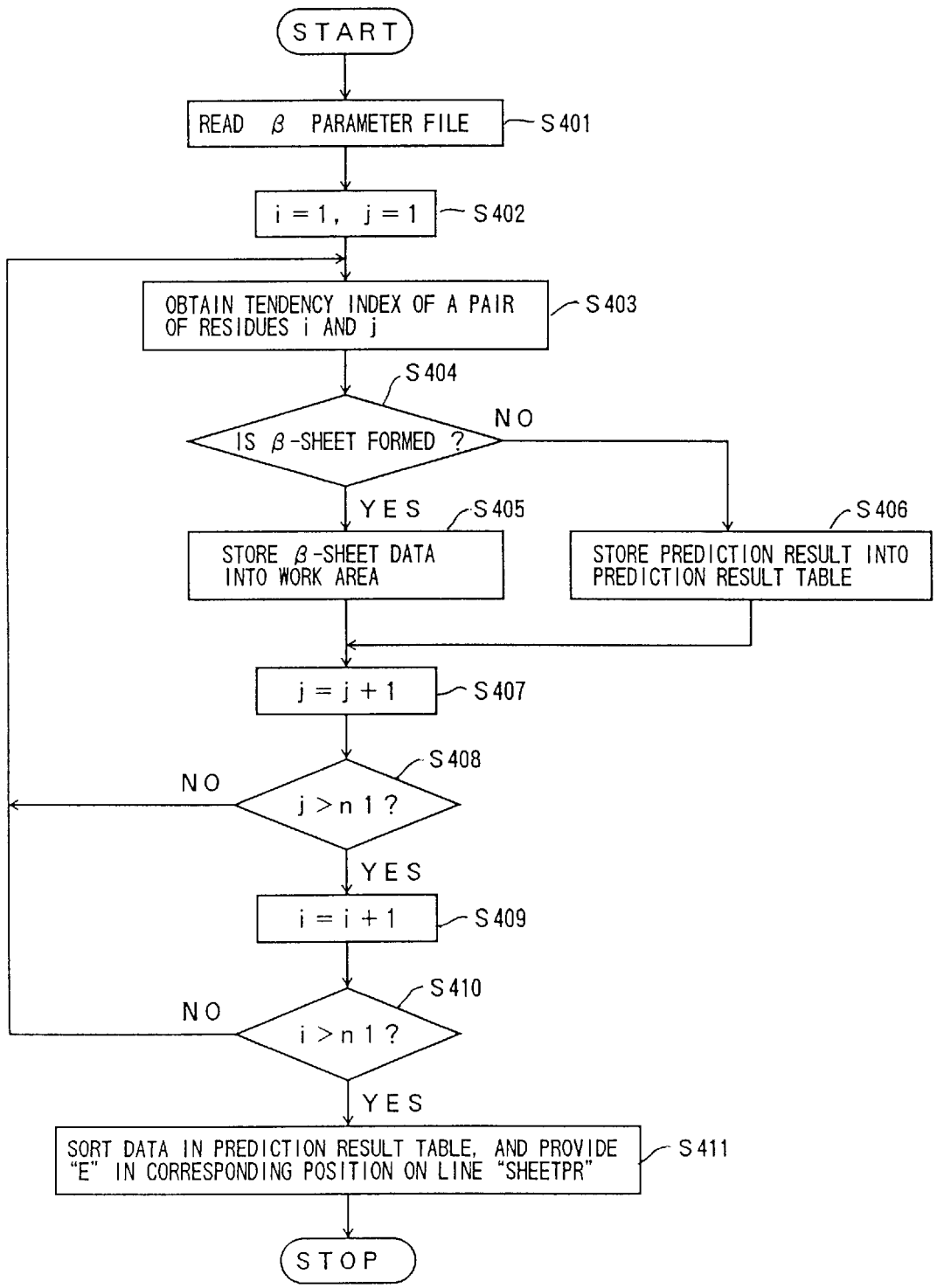
FIG. 11 is a flowchart of a β-sheet prediction operation performed by a β-sheet prediction unit shown in FIG. 4.

A description will now be given of an operation for prediction of the β-sheet in the above-mentioned step S400. FIG. 11 is a flowchart of the β-sheet prediction operation performed by the β-sheet prediction unit 120.

When the β-sheet prediction operation is started, the β-sheet prediction unit 120 reads, in step S401, the contents of the work area in which the residue data corresponding to the residues not forming the α-helix are stored. At this time, the number of residues n1 is also read from the work area. The β-sheet prediction unit 12 also reads the β parameter file 220.

In step S402, the counter i is set to 1, and a counter j is set to 1. The counter j represents the number of positions from the value of the counter i. In the β-sheet prediction operation, a pair of residues corresponding to the positions i and j is processed.

In step S403, the tendency index of the pair of residues corresponding to the positions i and j is obtained from the β parameter file 220. At this time, the residue corresponding to the position i is assumed to be an N terminal, and the residue corresponding to the position j is assumed to be a C terminal. For example, in the example shown in FIG. 6, if the residue i is G, and the residue j is R, the tendency index is "0.3".

In step S404, it is determined whether or not the pair of residues i and j forms the β-sheet by comparing the tendency index with a predetermined threshold value "th". The threshold value "th" is equal to 1, for example. That is, if the tendency index exceeds the threshold value, it is determined that the β-sheet is formed, and if not, it is determined that the β-sheet is not formed.

If it is determined, in step S404, that the β-sheet is formed, the routine proceeds to step S405. In step S405, the β-sheet data is stored in the work area when the β-sheet is consecutively formed and until the consecutiveness is interrupted, and then the routine proceeds to step S407. On the other hand if, it is determined, in step S404, that the β-sheet is not formed, the routine proceeds to step S406. In step S406, if the prediction result is stored in the work area, the residue data is stored in a prediction result table shown below.

| Pos. No. | Res. No. N-term. | Res. Seq. N-term. | Res. No. C-term. | Res. Seq. C-term. | Number of "E" |
|---|---|---|---|---|---|
| 1 | 10–11 | VQ | 51–52 | CS | 2 |
| 2 | 25–28 | NSCI | 93–96 | FYKH | 4 |
| 3 | 33–35 | SCV | 111–113 | VAH | 3 |
| 4 | 134 | C | 99 | A | 1 |

In step 407, the counter j is incremented (j=j+1).

In step S408, it is determined whether or not j is greater than the value n1. If j is not greater than n1, the routine returns to step S403. If j is greater than n1, the routine proceeds to step S409. In step 409, the counter i is incremented (i=i+1). It is then determined, in step S410, whether or not i is greater than n1 in the work area. If i is not greater than n1, the routine returns to step S403. If i is greater that n1, the routine proceeds to step S411.

In step S411, the data in the prediction result table is sorted and rearranged in accordance with an order in which the data having the maximum number of consecutive residues determined to form the β-sheets (marks "E") is positioned first. Then, the mark "E" is provided in positions corresponding to the residues at the first position in the prediction result table on a line "SHEETPR" in the result file. In the case of the above-mentioned prediction result table, the data is rearranged in the order of the position number "2", "3", "1", "4".

As discussed above, the tendency index of the β-sheet is investigated for each residue, and the mark "E" is stored in the work area only when the tendency index is greater than the threshold value. When the consecutiveness of the mark "E" is interrupted, the data is transferred to the above-mentioned prediction result table, and then the data in the table is sorted according to the number of the marks "E".

Figure 12:
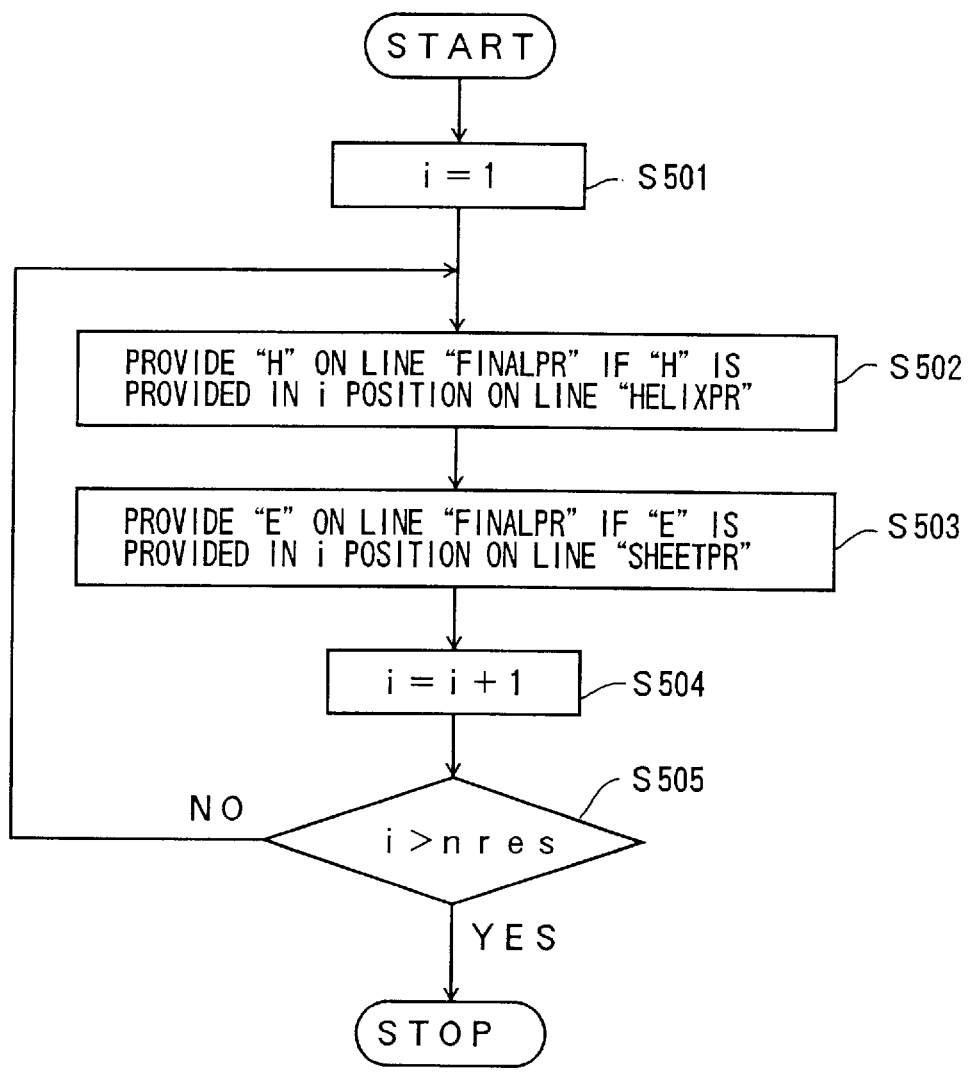
FIG. 12 is a flowchart of a secondary structure prediction result producing operation performed by a prediction result combining unit shown in FIG. 4.

A description will now be given of an operation for producing the result of prediction of the secondary structure. FIG. 12 is a flowchart of the secondary structure prediction result producing operation performed by the prediction result combining unit 130.

When the secondary structure prediction result producing operation is started, the counter i is set to 1 in step S501. Then, in step S502, if the mark "H" is provided in the i position on a line "HELIXPT" in the result file shown in FIG. 8, the mark "H" is provided on a line "FINALPR" in the result file. In step S503, if the mark "E" is provided in the i position on the line "SHEETPR" in the result file shown in FIG. 8, the mark "E" is provided on the line "FINALPR" in the result file.

In step S504, the counter i is incremented. It is determined, in step S505, whether or not the counter i is greater than the number "nres" of all of the residues. If it is determined that i is not greater than "nres", the routine returns to step S502. If i is greater than nres, the routine is ended.

By performing the secondary structure prediction result producing operation, contents of the result file shown in FIG. 8 are obtained. It should be noted that data provided on a line "SUMMARY" represent results of experiments by an X-ray crystallographic analysis or an NMR analysis. This line is provided for reference only, and is not needed for the present invention.

A further description will now be given, with reference to FIGS. 5, 7 and 10, of the α-helix prediction operation of the present embodiment. When the formation of the α-helix is determined, only the α-helix is sought by using a neural network from amino acid sequence (SEQUENCE).

Figure 13:
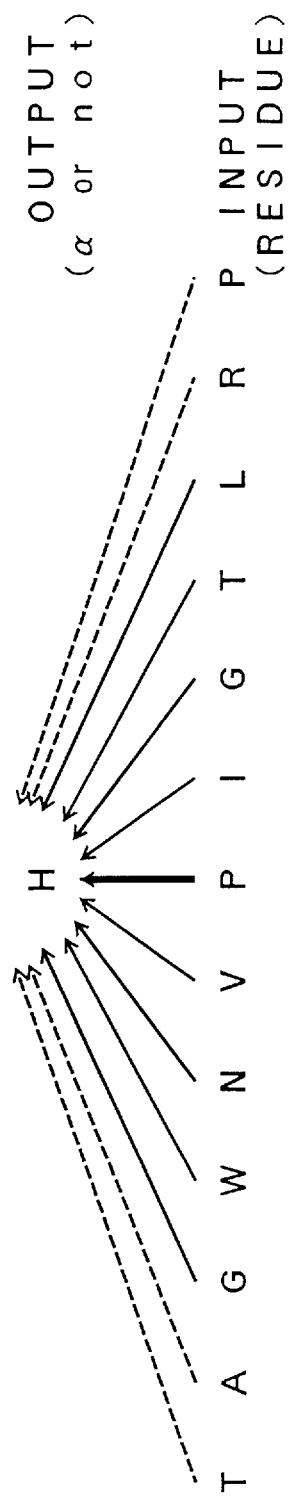
FIG. 13 is an illustration for explaining a tendency of an α-helix.

As shown in FIG. 13, it is previously determined whether various types of residues can form the α-helix. The determination results are learned by the neural network. Accordingly, it can be determined whether or not the type of given amino acid residue based on the calculated α-helix index can form the α-helix. When the sequence "T,A,G,W, N,V,P,I,G,T,L,R,P" of amino acid residues shown in FIG. 13 is supplied, an α-helix formation index of the center residue is calculated by using the neural network by referring to the weight values shown in FIG. 5. In this case, the center residue P most influences the α-helix formation index. The residues V and I influences the α-helix formation index next. That is, magnitude of influence to the α-helix formation is varied in accordance with a distance from the center residue P. This relates to the process of step S303 in FIG. 10.

When the value of the α-helix formation index is greater than a predetermined value, for example, a value of 0.0, it is determined that the α-helix is formed. This relates to the process of step S304. If it is determined that the α-helix is formed, a formation index is formed, the mark "H" is provided in a corresponding position on a line "HELIXPT" in a work area shown in FIG. 14. In FIG. 14 marks "H" are provided in positions corresponding to residues "S,N,P,E,A, T,K,C,F,W,Q,R,N,M,R,K,C,I,Q,A,I,A" among residues described on a line "SEQUENCE". This relates to the process of step S305.

Then, it is determined whether or not the mark "H" is provided in consecutive positions in a single unit. In this case, the single unit comprises four consecutive positions. In the case shown in FIG. 14, this condition is satisfied by series of residues "S,N,P,E,A,T,K,C,F", "W,Q,R,N,M,R,K" and "C,I,Q,A,I,A". The marks "H", which are not included in an area of more than four consecutive positions provided with the mark "H", are deleted. This relates to the process of step S308. Thereafter, the residue data corresponding to the deleted marks "H" is stored in the work area. This relates to the process of step S310.

A further description will now be given of the β-sheet prediction operation according to the present embodiment.

Figure 15:
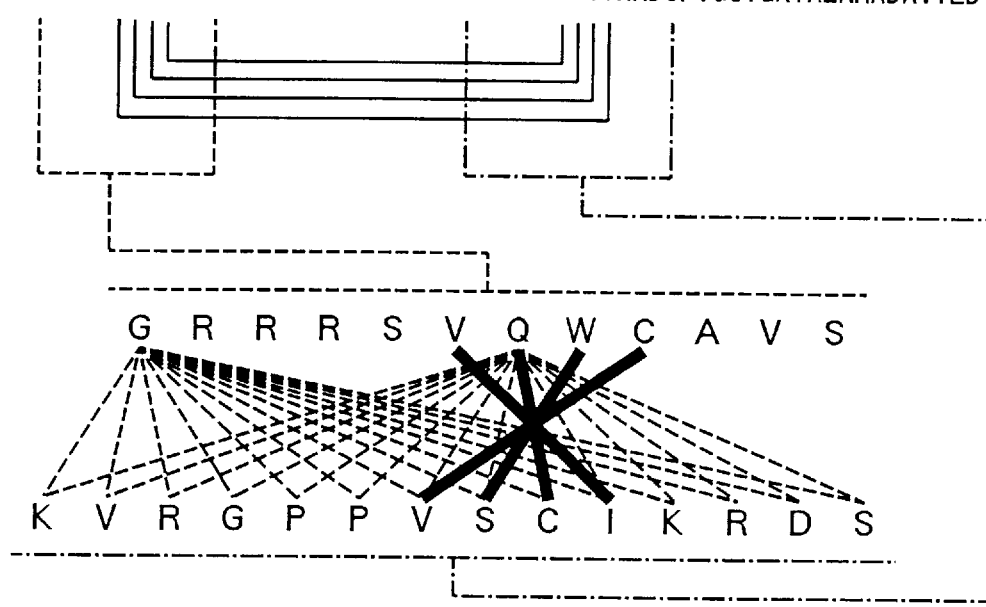
FIG. 15 is an illustration for explaining a prediction of a β-sheet.

The tendency of the β-sheet is investigated for all pairs of amino acid residues which were predicted not to form the α-helix by the above-mentioned α-helix prediction operation by using the values in the β-sheet parameter file shown in FIG. 6. In the example shown in FIG. 15, the tendency index between the residues V and I is determined as "2.8" and the tendency index between the residues Q and C is determined as "1.5" by referring to the β-sheet parameter file. In FIG. 15, a line "SHEETPR" is provided for indicating the results of the β-sheet prediction operation, and other lines are similar to those described with respect to the α-helix prediction operation. In FIG. 15, dashed lines and bold lines indicate that the investigation on the β-sheet tendency index is performed for all residues by the round-robin method. The bold lines indicate the pairs of residues which have high β-sheet tendency indexes. Accordingly, the series of residues "V,Q,W,C" and "V,S,C,I" are predicted to form the β-sheet, and thus the marks "E" are provided in the corresponding positions on the line "SHEETPR".

Figure 16:
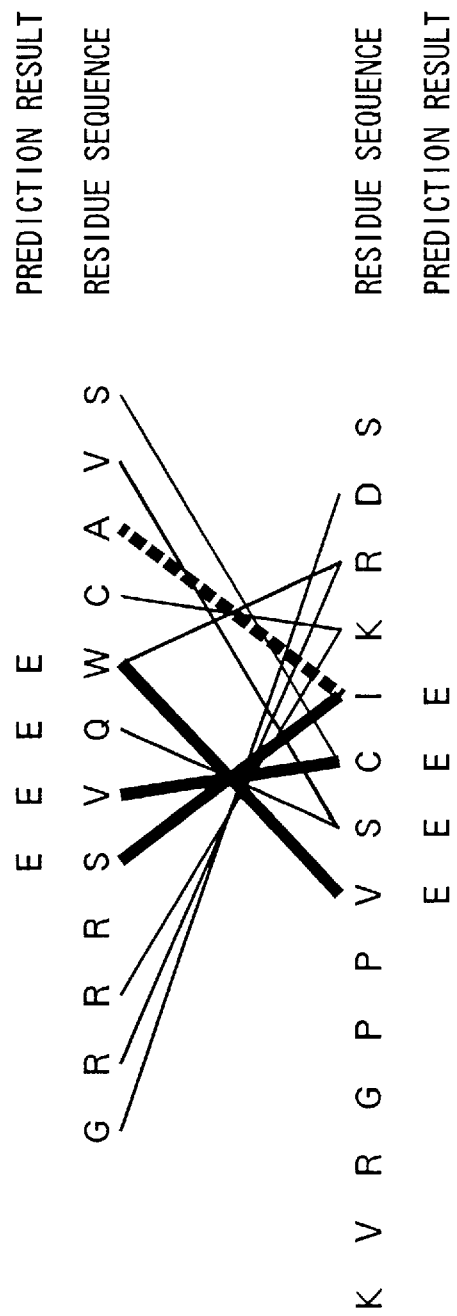
FIG. 16 is an illustration for explaining a selection of candidates for the β-sheet.

The above-mentioned process is applied for all pairs of the residues which were predicted as not to form the α-helix so as to seek pairs of residues having the β-sheet tendency indexes greater than the predetermined threshold value. Then, pairs of residues having more than two consecutive residues are selected as candidates for the β-sheet. At this time, if there is a series of pairs having the β-sheet greater than the threshold value including therein a single pair (Q,S) having the β-sheet not greater than the threshold value, the series of pairs is regarded as consecutive pairs. In FIG. 16, bold lines indicate pairs of residues having the β-sheet tendency indexes greater than the threshold value; thin lines indicate pairs of residues having the β-sheet tendency indexes less than the threshold value; dashed lines indicate pairs of residues having no consecutive residues which are candidates for the β-sheet.

A description will now be given of an output operation of the secondary structure prediction result according to the present embodiment. FIG. 17 is an illustration for explaining the output operation of the secondary structure prediction result according to the present embodiment. An example shown in FIG. 17 is obtained by combining the α-helix prediction result as shown in FIG. 14 with the β-sheet prediction result as shown in FIG. 15. In FIG. 17, a line "FINALPR" indicates a final result of the secondary structure prediction which is obtained by copying a line "HELIXPT" to the line "FINALPR" and then overlapping a line "SHEETPR" to the "FINALPR".

It should be noted that a line "SUMMARY" in FIGS. 14, 15 and 17 indicates a result obtained by an X-ray crystallographic analysis or an NMR analysis. Accordingly, it is preferable that the result is very similar to the result indicated on the line "SUMMARY".

The prediction result combining unit 130 of the structure prediction unit 100 stores the prediction result into the result file 240. This file can be read by a user for practical use, or the contents of the file can be displayed on a screen.

In the above-mentioned embodiment, the mark ("E") representing the β-sheet is provided when the β-sheet is predicted, and the mark is written in the prediction result table when the consecutiveness of the mark is interrupted. However, the present invention is not limited to this structure. For example, the data may be written in the prediction result table when the mark is not provided two consecutive times. In this case, when a condition occurs where the mark is not provided one time, the mark is automatically and forcibly provided so as to regard the series of residues having a single residue not provided with the mark as a series of consecutive residues. It should be noted that the number of times the mark is not provided can be arbitrarily determined. However, one time may be appropriate because a large number of times may decrease an accuracy of prediction.

The above-mentioned embodiment was described in relation to the system in which the interim results are temporarily stored in the work area of the memory. The interim result may be stored into a file provided in an external device.

As mentioned above, according to the present embodiment, a secondary structure prediction having a high accuracy can be performed by a simple signal operation with respect to the prediction of an α-helix and the prediction of a β-sheet which was difficult by a conventional method.

Accordingly, prediction of the secondary structure including the α-helix and the β-sheet can be performed by a simple manner by inputting sequence data of various protein, such as an ALL-α protein, an ALL-β protein, an α/β protein or an α+β protein, to the sequence file 230, and then inputting the data to the structure prediction unit 100. Thus, the prediction system according to the present invention can be used commonly for various types of proteins by merely preparing data to be input to the sequence file 230.

The present invention is not limited to the specifically disclosed embodiments, and variations and modifications may be made without departing from the scope of the present invention.

What is claimed is:

1. A method for predicting secondary structures which are characteristic structures of a protein including an α-helix and a β-sheet, comprising the steps of:
    a) predicting a formation of the α-helix with respect to each amino acid residue in a sequence;
    b) predicting a formation of the β-sheet with respect to all pairs of amino acid residues which are not predicted to form the α-helix by step a); and
    c) combining results obtained by step a) and step b) to obtain a result of prediction of the secondary structures of the protein,
    wherein the step a) comprises the steps of:
    a-1) learning which types of amino acid residues have a tendency to form the α-helix;
    a-2) determining the formation of the α-helix with respect to each amino acid residue in said sequence based on results obtained by step a-1); and
    a-3) providing a mark to each amino acid residue which was determined to form the α-helix by step a-2), and subjecting all of the amino acid residues determined not to form the α-helix by step a-2) to the prediction of the β-sheet, and
    wherein a determination of step a-2) is made based on consecutiveness of the amino acid residues having a predetermined level of formability of the α-helix.

2. The method as claimed in claim 1, wherein the consecutiveness of the amino acid residues is determined based on a series of amino acid residues comprising four amino acid residues.

3. A method for predicting secondary structures which are characteristic structures of a protein including an α-helix and a β-sheet, comprising the steps of:
    a) predicting a formation of the α-helix with respect to each amino acid residue in a sequence;
    b) predicting a formation of the β-sheet with respect to all pairs of amino acid residues which are not predicted to form the α-helix by step a); and
    c) combining results obtained by step a) and step b) to obtain a result of prediction of the secondary structures of the protein,
    wherein the step b) comprises the steps of:
    b-1) determining a β-sheet tendency index with respect to all pairs of amino acid residues which were not predicted to form the α-helix by the step a);
    b-2) selecting candidate amino acid residues forming the β-sheet by comparing the β-sheet tendency index with a predetermined threshold value, amino acid residues of a pair having a β-sheet tendency index greater than the threshold value being selected as the candidate amino acid residues; and
    b-3) seeking a series of candidate amino acid residues comprising a maximum number of candidate amino acid residues from among the candidate residues selected by step b-2) so that said series of candidate amino acid residues is determined to form the β-sheet.

4. The method as claimed in claim 3, wherein in step b-3), when less than a predetermined number of consecutive amino acid residues is not selected as the candidate amino acid residues, said non-selected consecutive amino acid residues are regarded as the amino acid residues forming the β-sheet.

5. An apparatus for predicting secondary structures which are characteristic structures of a protein including an α-helix and a β-sheet, said apparatus comprising:

α-helix predicting means for predicting a formation of the α-helix with respect to each amino acid residue in a sequence;

β-sheet predicting means for predicting a formation of the β-sheet with respect to all pairs of amino acid residues which were not predicted to form the α-helix by said α-helix predicting means; and combining means for combining results obtained by said α-helix predicting means and said β-sheet predicting means to obtain a result of prediction of the secondary structure of the protein, wherein said α-helix predicting means comprises:

learning means for learning which types of amino acid residues have a tendency to form the α-helix;

determining means for determining the formation of the α-helix with respect to each amino acid residue in said sequence based on results obtained by said learning means; and providing means for providing a mark to each residue which was determined to form the α-helix by said determining means, and subjecting all of the residues determined not to form the α-helix by said determining means to the prediction of the β-sheet; and wherein a determination by said determining means is made based on consecutiveness of the residues having a predetermined level of formability of the α-helix.

6. An apparatus for predicting secondary structures which are characteristic structures of a protein including an α-helix and a β-sheet, said apparatus comprising:

α-helix predicting means for predicting a formation of the α-helix with respect to each amino acid residue in a sequence;

β-sheet predicting means for predicting a formation of the β-sheet with respect to all pairs of amino acid residues which were not predicted to form the α-helix by said α-helix predicting means; and combining means for combining results obtained by said α-helix predicting means and said β-sheet predicting means to obtain a result of prediction of the secondary structure of the protein, wherein said α-helix predicting means comprises:

learning means for learning which types of amino acid residues have a tendency to form the α-helix;

determining means for determining the formation of the α-helix with respect to each amino acid residue in said sequence based on results obtained by said learning means; and providing means for providing a mark to each residue which was determined to form the α-helix by said determining means, and subjecting all of the residues determined not to form the α-helix by said determining means to the prediction of the β-sheet;

wherein a determination by said determining means is made based on consecutiveness of the residues having a predetermined level of formability of the α-helix, and wherein the consecutiveness of the residues is determined based on a series of residues comprising four residues.

7. An apparatus for predicting secondary structures which are characteristic structures of a protein including an α-helix and a β-sheet, said apparatus comprising:

α-helix predicting means for predicting a formation of the α-helix with respect to each amino acid residue in a sequence;

β-sheet predicting means for predicting a formation of the β-sheet with respect to all pairs of amino acid residues which were not predicted to form the α-helix by said α-helix predicting means; and combining means for combining results obtained by said α-helix predicting means and said β-sheet predicting means to obtain a result of prediction of the secondary structure of the protein, wherein said β-sheet predicting means comprises:

determining means for determining a β-sheet tendency index with respect to all pairs of residues which were not predicted to form the α-helix by said α-helix predicting means;

selecting means for selecting candidate residues forming the β-sheet by comparing the β-sheet tendency index with a predetermined threshold value, residues of a pair having a β-sheet tendency index greater than the threshold value being selected as the candidate residues; and seeking means for seeking a series of candidate residues comprising a maximum number of candidate residues from among the candidate residues selected by said selecting means so that said series of candidate residues is determined to form the β-sheet.

8. The apparatus as claimed in claim 7, wherein when less than a predetermined number of consecutive residues is not selected as the candidate residues, said non-selected consecutive residues are regarded as the residues forming the β-sheet.

9. A method for predicting secondary structures which are characteristic structures of a protein including an α-helix and a β-sheet, comprising the steps of:

a) predicting a formation of the α-helix with respect to each amino acid residue in a sequence;

b) predicting a formation of the β-sheet with respect to all pairs of amino acid residues which are not predicted to form the α-helix by step a); and c) combining results obtained by step a) and step b) to obtain a result of prediction of the secondary structures of the protein, wherein the step a) includes the steps of:

a-1) learning which types of amino acid residues have a tendency to form the α-helix;

a-2) determining the formation of the α-helix with respect to each amino acid residue in said sequence based on results obtained by step a-1); and a-3) providing a mark to each amino acid residue which was determined to form the α-helix by step a-2), and subjecting all of the amino acid residues determined not to form the α-helix by step a-2) to the prediction of the β-sheet, and wherein the step b) includes the steps of:

b-1) determining a β-sheet tendency index with respect to all pairs of amino acid residues which were not predicted to form the α-helix by the step a);

b-2) selecting candidate amino acid residues forming the β-sheet by comparing the β-sheet tendency index with a predetermined threshold value, amino acid residues of a pair having a β-sheet tendency index greater than the threshold value being selected as the candidate amino acid residues; and b-3) seeking a series of candidate amino acid residues comprising a maximum number of candidate amino acid residues from among the candidate residues selected by step b-2) so that said series of candidate amino acid residues is determined to form the β-sheet.

10. The method as claimed in claim 9, wherein a determination of step a-2) is made based on consecutiveness of the amino acid residues having a predetermined level of formability of the α-helix.

11. The method as claimed in claim 10, wherein the consecutiveness of the amino acid residues is determined based on a series of amino acid residues comprising four amino acid residues.

12. The method as claimed in claim 9, wherein in step b-3), when less than a predetermined number of consecutive amino acid residues is not selected as the candidate amino acid residues, said non-selected consecutive amino acid residues are regarded as the amino acid residues forming the β-sheet.

13. An apparatus for predicting secondary structures which are characteristic structures of a protein including an α-helix and a β-sheet, said apparatus comprising:

α-helix predicting means for predicting a formation of the α-helix with respect to each amino acid residue in a sequence;

β-sheet predicting means for predicting a formation of the β-sheet with respect to all pairs of amino acid residues which were not predicted to form the α-helix by said α-helix predicting means; and combining means for combining results obtained by said α-helix predicting means and said β-sheet predicting means to obtain a result of prediction of the secondary structure of the protein, wherein said α-helix predicting means comprises:

learning means for learning which types of amino acid residues have a tendency to form the α-helix;

determining means for determining the formation of the α-helix with respect to each amino acid residue in said sequence based on results obtained by said learning means; and providing means for providing a mark to each residue which was determined to form the α-helix by said determining means, and subjecting all of the residues determined not to form the α-helix by said determining means to the prediction of the β-sheet, and wherein said β-sheet predicting means comprises:

determining means for determining a β-sheet tendency index with respect to all pairs of residues which were not predicted to form the α-helix by said α-helix predicting means;

selecting means for selecting candidate residues forming the β-sheet by comparing the β-sheet tendency index with a predetermined threshold value, residues of a pair having a β-sheet tendency index greater than the threshold value being selected as the candidate residues; and seeking means for seeking a series of candidate residues comprising a maximum number of candidate residues from among the candidate residues selected by said selecting means so that said series of candidate residues is determined to form the β-sheet.

14. The apparatus as claimed in claim 13, wherein a determination by said determining means is made based on consecutiveness of the residues having a predetermined level of formability of the α-helix.

15. The apparatus as claimed in claim 14, wherein the consecutiveness of the residues is determined based on a series of residues comprising four residues.

16. The apparatus as claimed in claim 13, wherein when less than a predetermined number of consecutive residues is not selected as the candidate residues, said non-selected consecutive residues are regarded as the residues forming the β-sheet.

* * * * *